United States Patent
Ormsby et al.

(10) Patent No.: US 9,039,698 B2
(45) Date of Patent: May 26, 2015

(54) RADIO FREQUENCY ABLATION SYSTEM WITH TRACKING SENSOR

(75) Inventors: Theodore C. Ormsby, Milpitas, CA (US); Shen Gwo Jenn, Carlsbad, CA (US); George L. Leung, San Diego, CA (US)

(73) Assignee: Medwaves, Inc., San Diego, CA (US)

( * ) Notice: Subject to any disclaimer, the term of this patent is extended or adjusted under 35 U.S.C. 154(b) by 1029 days.

(21) Appl. No.: 12/953,879

(22) Filed: Nov. 24, 2010

(65) Prior Publication Data

US 2011/0130750 A1    Jun. 2, 2011

Related U.S. Application Data

(60) Provisional application No. 61/265,088, filed on Nov. 30, 2009.

(51) Int. Cl.
| | |
|---|---|
| A61B 18/14 | (2006.01) |
| A61B 18/18 | (2006.01) |
| A61B 18/00 | (2006.01) |
| A61B 19/00 | (2006.01) |

(52) U.S. Cl.
CPC ... *A61B 18/1815* (2013.01); *A61B 2018/00196* (2013.01); *A61B 2018/1853* (2013.01); *A61B 2018/1861* (2013.01); *A61B 2019/5251* (2013.01)

(58) Field of Classification Search
USPC ............ 606/32–35, 41, 45–50; 607/101–102; 600/424, 427, 433–435
See application file for complete search history.

(56) References Cited

U.S. PATENT DOCUMENTS

| | | |
|---|---|---|
| 3,309,455 A | 3/1967 | Mildner |
| 4,271,848 A | 6/1981 | Turner et al. |
| 4,408,089 A | 10/1983 | Nixon |
| 4,583,556 A | 4/1986 | Hines et al. |
| 4,776,086 A | 10/1988 | Kasevich et al. |

(Continued)

FOREIGN PATENT DOCUMENTS

| | | |
|---|---|---|
| EP | 1055399 | 11/2000 |
| WO | WO-96/05768 A1 | 2/1996 |

(Continued)

OTHER PUBLICATIONS

NDI Aurora Sensors & Tools, Feb. 2009, 4 pages.
(Continued)

*Primary Examiner* — Michael Peffley
(74) *Attorney, Agent, or Firm* — Cesari and McKenna, LLP

(57) ABSTRACT

An RF ablation system has a hollow conductive coaxial cable comprising inner and outer coaxial tubular conductors, and an ablating member mounted at the distal end portion of the cable for delivery of radio frequency energy including microwaves to the target body tissue. The inner conductor has a central lumen and extends at least up to the ablating member. At least one electromagnetic tracking sensor coil with a magnetic core is located in the central lumen at the distal end portion of the cable, close to the distal tip of the cable, and connected to a signal processing unit. An electromagnetic field generator positioned in the vicinity of a patient undergoing treatment generates an electromagnetic field which induces a voltage in the sensor coil. The signal processing unit uses the induced voltage to calculate the position and orientation of the distal end portion or tip of the catheter in a patient's body.

3 Claims, 4 Drawing Sheets

(56) References Cited

U.S. PATENT DOCUMENTS

| | | | |
|---|---|---|---|
| 5,099,845 A | 3/1992 | Besz et al. | |
| 5,150,717 A | 9/1992 | Rosen et al. | |
| 5,211,165 A | 5/1993 | Dumoulin et al. | |
| 5,275,597 A | 1/1994 | Higgins et al. | |
| 5,370,644 A | 12/1994 | Langberg | |
| 5,370,677 A | 12/1994 | Rudie et al. | |
| 5,425,367 A * | 6/1995 | Shapiro et al. | 600/424 |
| 5,462,545 A | 10/1995 | Wang et al. | |
| 5,500,012 A | 3/1996 | Brucker et al. | |
| 5,540,681 A | 7/1996 | Strul et al. | |
| 5,617,854 A | 4/1997 | Munsif | |
| 5,642,736 A | 7/1997 | Avitall | |
| 5,656,029 A | 8/1997 | Miran et al. | |
| 5,683,382 A | 11/1997 | Lenihan et al. | |
| 5,702,433 A | 12/1997 | Taylor et al. | |
| 5,727,553 A * | 3/1998 | Saad | 600/407 |
| 5,738,683 A | 4/1998 | Osypka | |
| 5,741,249 A * | 4/1998 | Moss et al. | 606/33 |
| 5,776,176 A | 7/1998 | Rudie | |
| 5,788,692 A | 8/1998 | Campbell et al. | |
| 5,842,984 A | 12/1998 | Avitall | |
| 5,849,028 A | 12/1998 | Chen | |
| 5,863,291 A | 1/1999 | Schaer | |
| 5,882,333 A | 3/1999 | Schaer et al. | |
| 5,893,885 A | 4/1999 | Webster, Jr. | |
| 5,902,251 A | 5/1999 | VanHooydonk | |
| 5,941,858 A * | 8/1999 | Johnson | 604/526 |
| 5,957,969 A | 9/1999 | Warner et al. | |
| 6,014,579 A | 1/2000 | Pomeranz et al. | |
| 6,033,403 A | 3/2000 | Tu et al. | |
| 6,071,280 A | 6/2000 | Edwards et al. | |
| 6,123,718 A | 9/2000 | Tu et al. | |
| 6,175,768 B1 | 1/2001 | Arndt et al. | |
| 6,190,382 B1 | 2/2001 | Ormsby | |
| 6,230,060 B1 | 5/2001 | Mawhinney | |
| 6,288,785 B1 | 9/2001 | Frantz et al. | |
| 6,319,250 B1 | 11/2001 | Falwell et al. | |
| 6,383,182 B1 | 5/2002 | Berube et al. | |
| 6,385,482 B1 | 5/2002 | Boksberger et al. | |
| 6,527,769 B2 | 3/2003 | Langberg | |
| 6,546,270 B1 * | 4/2003 | Goldin et al. | 600/374 |
| 6,553,326 B1 | 4/2003 | Kirsch et al. | |
| 6,592,581 B2 | 7/2003 | Bowe | |
| 6,610,058 B2 | 8/2003 | Flores | |
| 6,663,625 B1 | 12/2003 | Ormsby | |
| 6,669,692 B1 | 12/2003 | Nelson et al. | |
| 6,690,963 B2 * | 2/2004 | Ben-Haim et al. | 600/424 |
| 6,772,001 B2 * | 8/2004 | Maschke | 600/423 |
| 6,941,953 B2 | 9/2005 | Feld et al. | |
| 7,004,938 B2 * | 2/2006 | Ormsby et al. | 606/33 |
| 7,070,595 B2 | 7/2006 | Ormsby et al. | |
| 7,128,739 B2 * | 10/2006 | Prakash et al. | 606/33 |
| 7,229,450 B1 | 6/2007 | Chitre et al. | |
| 7,306,593 B2 * | 12/2007 | Keidar et al. | 606/34 |
| 7,594,913 B2 | 9/2009 | Ormsby et al. | |
| 7,623,899 B2 | 11/2009 | Worley et al. | |
| 8,152,799 B2 * | 4/2012 | Ormsby et al. | 606/33 |
| 2001/0018596 A1 | 8/2001 | Selmon et al. | |
| 2002/0087151 A1 | 7/2002 | Mody et al. | |
| 2003/0100894 A1 | 5/2003 | Mahon et al. | |
| 2005/0055019 A1 | 3/2005 | Skarda | |
| 2005/0059965 A1 | 3/2005 | Eberl et al. | |
| 2005/0090880 A1 | 4/2005 | Venturelli | |
| 2005/0222563 A1 | 10/2005 | McDaniel et al. | |
| 2006/0142752 A1 | 6/2006 | Ormsby et al. | |
| 2007/0066972 A1 * | 3/2007 | Ormsby et al. | 606/41 |
| 2008/0015570 A1 | 1/2008 | Ormsby | |
| 2009/0082762 A1 | 3/2009 | Ormsby | |
| 2009/0299360 A1 | 12/2009 | Ormsby | |
| 2010/0268219 A1 | 10/2010 | Ormsby | |
| 2011/0009858 A1 | 1/2011 | Ormsby | |

FOREIGN PATENT DOCUMENTS

| | | |
|---|---|---|
| WO | 9726544 | 7/1997 |
| WO | 0035363 | 6/2000 |
| WO | 0226146 | 4/2002 |
| WO | WO-03/047448 A1 | 6/2003 |

OTHER PUBLICATIONS

Office Action dated from U.S. Appl. No. 11/781,467 dated Jun. 23, 2011.

Notification, International Search Report and Written Opinion for PCT/US2010/058082 dated Aug. 18, 2011.

* cited by examiner

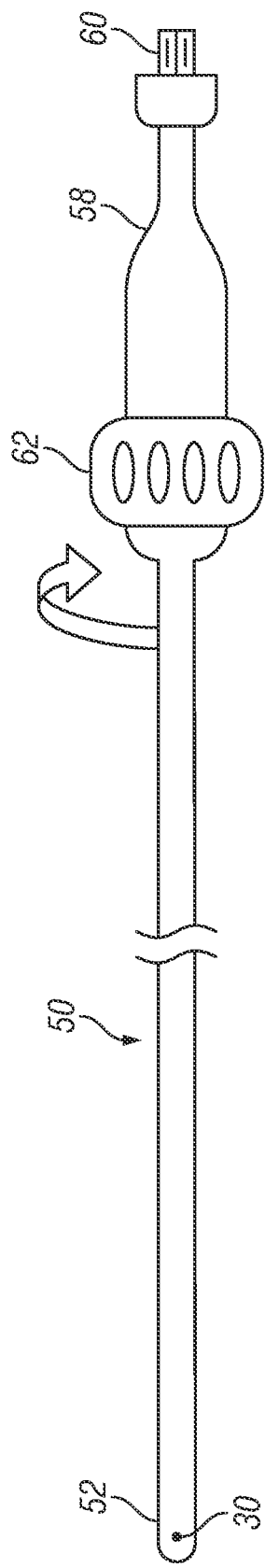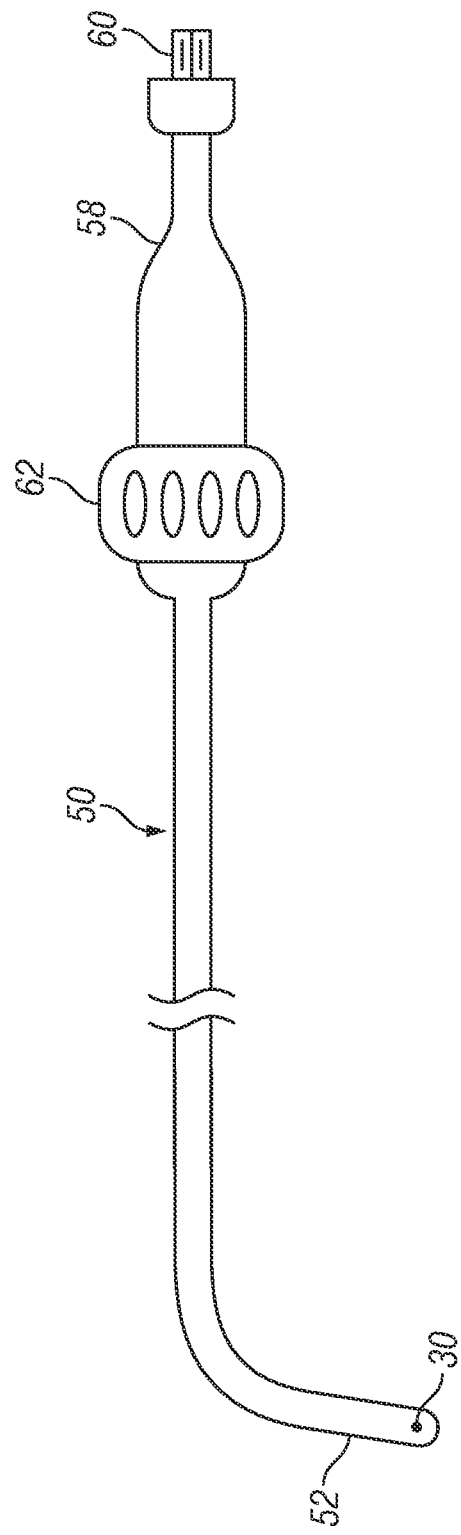

RADIO FREQUENCY ABLATION SYSTEM WITH TRACKING SENSOR

RELATED APPLICATION

The present application claims the benefit of U.S. provisional pat. App. Ser. No. 61/265,088, filed Nov. 30, 2009, the contents of which are incorporated herein by reference in their entirety.

BACKGROUND

1. Field of the Invention

The present invention generally relates to medical catheters which are used for the irradiation of biological tissues, such as devices for the ablation of biological tissues, and more particularly to such a device incorporating a tracking sensor.

2. Related Art

Catheters are used for a number of procedures, including diagnostic, therapeutic, and ablative procedures. In such procedures, a catheter is moved through a patient's body to a desired treatment site. Therapeutic issue ablation systems apply energy to a biological ablation tissue site via different energy exchange means, such as heat conduction and irradiation. These systems may employ various energy modes, such as radiofrequency, ultrasound, laser, cryogenic, and the like. Within the radio frequency (RF) range, certain microwave ablation systems are used to destroy or ablate biological tissues. In one application, a microwave ablation system is used to ablate cardiac tissues that cause irregular heartbeats or arrhythmia, avoiding the need for more risky and invasive open heart surgery. In such an application, an ablation member such as an RF antenna is incorporated as part of a catheter. The catheter is passed through the vein for access to the atrium. Within the atrium, the RF antenna is positioned at the desired location where ablation is applied. Microwave ablation systems can also be used in treatment of other biological sites such as arteries, organs and body vessels. As an example, a microwave ablation system may be used to ablate tumors in the lungs, liver, kidney or other areas of the body.

These surgical and therapeutic applications require an efficient system for the transmission of radio frequency energy to the ablating member for the delivery of energy to the target tissue site. U.S. Patent Application Publication No. 20080015570 of Ormsby et al. describes a tissue ablation system comprising a hollow conductive coaxial cable having a first inner elongated electrically conductive tubular member having a distal end portion, the first tubular member having a hollow, axially extending lumen, a second elongated electrically conductive member disposed in a substantially coaxial relationship over at least a portion of the first electrically conductive tubular member over substantially the length of the cable, a dielectric medium disposed between the first and second electrically conductive tubular members, and an ablating member or radio-frequency antenna which delivers radio frequency energy including microwaves to body tissue disposed at the distal end portion of the cable. The radio-frequency antenna is adapted to receive and irradiate radio-frequency energy in the microwave range at a frequency typically greater than 300 Megahertz (MHz) in the electromagnetic spectrum for ablating biological tissue along a biological ablation pathway.

Radio frequency tissue ablation devices for surgical and therapeutic applications also require an accurate system for positioning the ablation device in the vicinity of the target tissue site. In typical procedures, X-ray fluoroscopy is used to locate the position of the distal end portion of the catheter and to display real time images of the site to medical personnel performing the procedure. Because these images are static and two dimensional, surgeons typically require many views to interpret the actual position in the body, and such positioning systems, taken alone, are subject to errors and incorrect interpretation. Such systems also expose the patient and medical personnel conducting the procedure to relatively high amounts of radiation.

SUMMARY

Embodiments described herein provide for a radio-frequency catheter with an ablation device at its distal end for delivery of radio frequency energy to target body tissue, and a tracking sensor incorporated in the distal end portion of the catheter.

In one embodiment, a hollow conductive coaxial cable is provided, which comprises a first inner elongated electrically conductive tubular member having an axially extending lumen or passageway, and a second elongated electrically conductive member disposed in a substantially coaxial relationship over at least a portion of the first electrically conductive tubular member. Between the inner and outer conductive members, a dielectric medium is provided. At the distal end portion of the cable, an ablating member is mounted for the delivery of radio frequency energy including microwaves to the target body tissue. At least one electromagnetic tracking sensor coil with a magnetic core is located at the distal end portion of the cable, close to the distal tip of the catheter. In one embodiment, the ablating member is a monopole or dipole antenna extending up to the distal tip, and the sensor coil is located in the lumen close to the antenna. In another embodiment, the ablating member is a helical coil antenna at the distal end portion of the cable. The tracking sensor coil may be located within the helical coil antenna, or the antenna itself may also comprise the tracking sensor coil, with the magnetic core located within the coil antenna.

In one embodiment, conductive wires extend from the coil within the lumen to terminals in a handle at the proximal end of the catheter. The terminals are connected to a signal processing unit. An electromagnetic field generator positioned in the vicinity of a patient undergoing treatment generates an electromagnetic field which induces a voltage in the sensor coil. The signal processing unit uses the induced voltage to calculate the position and orientation of the distal end portion or tip of the catheter in a patient's body.

In one embodiment, reference coils connected to the signal processing unit may be located at fixed locations on an operating table or the like, and the induced voltages in these coils may be compared to the voltage induced in the coil located at the distal tip of the catheter, to aid in position determination.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which:

FIGS. 3A and 3B are side-elevational views of a deflectable RF ablation catheter according to another embodiment including a tracking sensor for use with the location tracking system of FIG. 1, with FIG. 3B illustrating the distal end portion of the catheter in a deflected condition;

DETAILED DESCRIPTION

Certain embodiments as disclosed herein provide for an ablation catheter including a location tracking system.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention.

Figure 1:
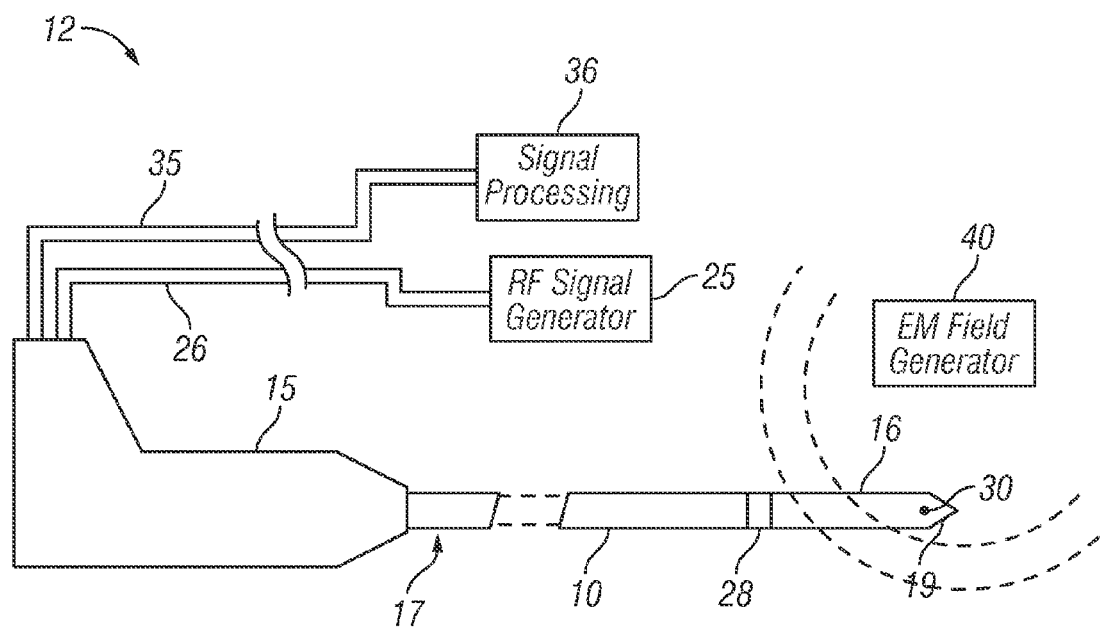
FIG. 1 is a schematic block diagram, partly broken away, of one embodiment of an ablation catheter system including a location tracking system.
Figure 2:
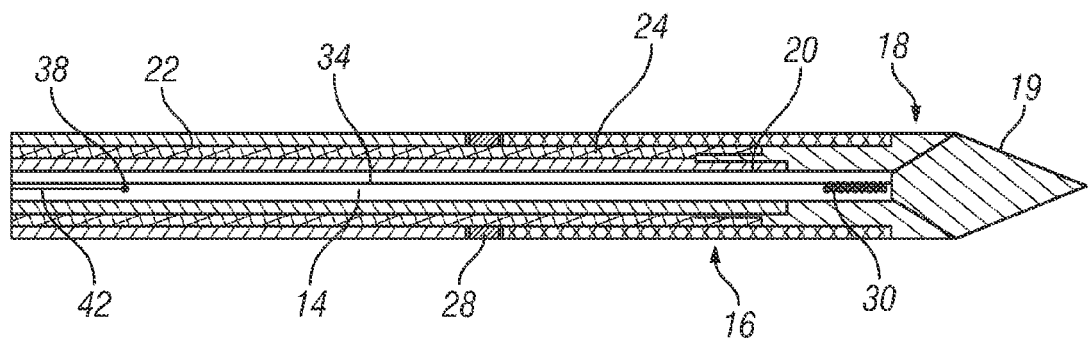
FIG. 2 is an enlarged cross-sectional view through the distal end portion of the catheter in FIG. 1.

FIGS. 1 and 2 illustrate a first embodiment of a radio frequency (RF) wave guide device or probe 10 forming part of a microwave ablation and position tracking system 12. The microwave ablation system is similar to that described in co-pending application Ser. No. 11/781,467 filed on Jul. 23, 2007, Ser. No. 11/858,736 filed on Sep. 20, 2007, and Ser. No. 12/424,287 filed on Apr. 15, 2009, the contents of each of which are incorporated herein by reference. Device 10 is generally tubular and has a multi-layer or coaxial cable construction with a central bore or lumen 14 (FIG. 2) extending along its length from a proximal portion 17 adjacent handle 15 to distal portion 16. A radio frequency (RF) ablation antenna 18 with an antenna tip 19 is located at the distal end portion of the device. Inner and outer electrically conductive tubular members or coaxial conductors 20, 22 extend coaxially from the proximal portion of the apparatus, with at least the inner conductor extending up to a location close to the distal end or tip 19 of the antenna. The inner conductor may be non-tubular in alternative embodiments. An RF transmission wave guide is defined between the inner and outer conductors. An outer jacket or casing (not illustrated) of dielectric polymer material encloses the co-axial conductors along at least a major portion of the length of the device 10.

The inner and outer conductors each comprise an elongated electrically conductive tubular member, with the outer conductor arranged in a substantially coaxial relationship over at least a portion of length of the inner conductor. This arrangement defines an annular space 24 between the walls of the inner and outer conductors where a dielectric medium is placed. The dielectric medium may be a solid or a fluid or a combination of solid and fluid which fill the space between the inner and outer conductor. Any unfilled space may be evacuated to form a vacuum or filled with an alternative dielectric solid or fluid material. A dielectric fluid medium such as air may be dispensed in lieu of a solid dielectric layer. Vacuum, which also exhibits dielectric property, may be introduced by the evacuation of air and sealing the space between the distal and proximal end portions of the cable during manufacture. Alternately, a vacuum source may be configured in fluid communication with the space between the inner and outer conductors.

The ablation antenna 18 located at the distal portion 10 of the apparatus may be a monopole or dipole antenna or a helical coil antenna, which is electrically coupled to at least the inner conductor of the coaxial cable device. The antenna is adapted to receive and radiate electromagnetic energy from a source of radio frequency energy 25 coupled with the inner and outer coaxial conductors via cable 26. In alternative embodiments, other forms of ablation devices or radio frequency antennas may be used in place of the antenna, such as a pair of spaced electrically conductive microstrips disposed at the distal end portion of the coaxial cable device, as described in U.S. Pat. No. 6,663,625, the contents of which are incorporated herein by reference. In one arrangement, the ablation antenna is coated with a single layer of dielectric encapsulant material. In other arrangements, various dielectric media may be used to control coupling of the ablation signal into the surrounding tissue, as described in co-pending application Ser. No. 12/424,287 referenced above, which was filed on Apr. 15, 2009.

In the embodiment of FIG. 2, antenna 18 is a monopole antenna with a pointed end or tip 19, and is secured to the distal end of the waveguide with a spacer or dielectric gap 28 between the distal end of outer conductor 22 and the opposing end face of the antenna. The inner conductor 20 has a distal end portion which projects into the antenna. An electromagnetic tracking sensor coil 30 with a magnetic core is located in the distal end portion 32 of the central hollow lumen 14 within the antenna, as illustrated in FIG. 2, and a twisted pair of conductive wires 34 extend from coil 30 through the lumen 14 from the distal end portion to the proximal end of the coaxial cable, where they are connected to terminals within the handle 15, and from there via cable 35 to a signal processing unit 36. A temperature sensor 38 may also be located within the central hollow lumen 14, and connected by conductive wires 42 to terminals in handle 15, and from handle 15 to signal processing unit via signal cable 35 or a second signal cable (not illustrated). Temperature signals may be processed as described in co-pending U.S. patent application Ser. No. 11/781,467 filed on Jul. 23, 2007 (US Pat. App. Pub. No. 2008/0015570), the contents of which are incorporated herein by reference.

The system 12 also includes an electromagnetic field generator 40 which generates an electromagnetic field, inducing a voltage in tracking sensor coil 30. The induced voltage is used by a measurement system in signal processing unit 36 to calculate the position and orientation of the antenna tip 19 in a patient's body. Additional reference coils may be located at fixed positions in the vicinity of the patient, for example at the corners of an operating table, and voltages induced in these coils may be used by the measurement system in calculating the position of coil 30. In one embodiment, the coil 30 and any reference coils may be Aurora™ sensors manufactured by Northern Digital, Inc. of Ontario, Canada. The system may also use the Aurora™ system control unit as part of processing unit 36, and the EM field generator may be an Aurora™ field generator. The Aurora™ sensor coils are miniature coils which may be easily incorporated in the central lumen of a coaxial catheter as illustrated in FIG. 2.

In embodiments where the antenna is a helical coil antenna, it is anticipated that the antenna itself may alternatively be used as a tracking sensor. In this case, the antenna coil is provided with a magnetic core, and is alternately connected to the RF signal generator while the EM field generator is off, and to the signal processing unit with the RF signal generator turned off and the EM field generator on. The tracking system may be used to position the tip of the antenna at the desired location in a patient's body, and may then be turned off while the RF signal generator is actuated to apply RF energy at the treatment site.

Figure 4:
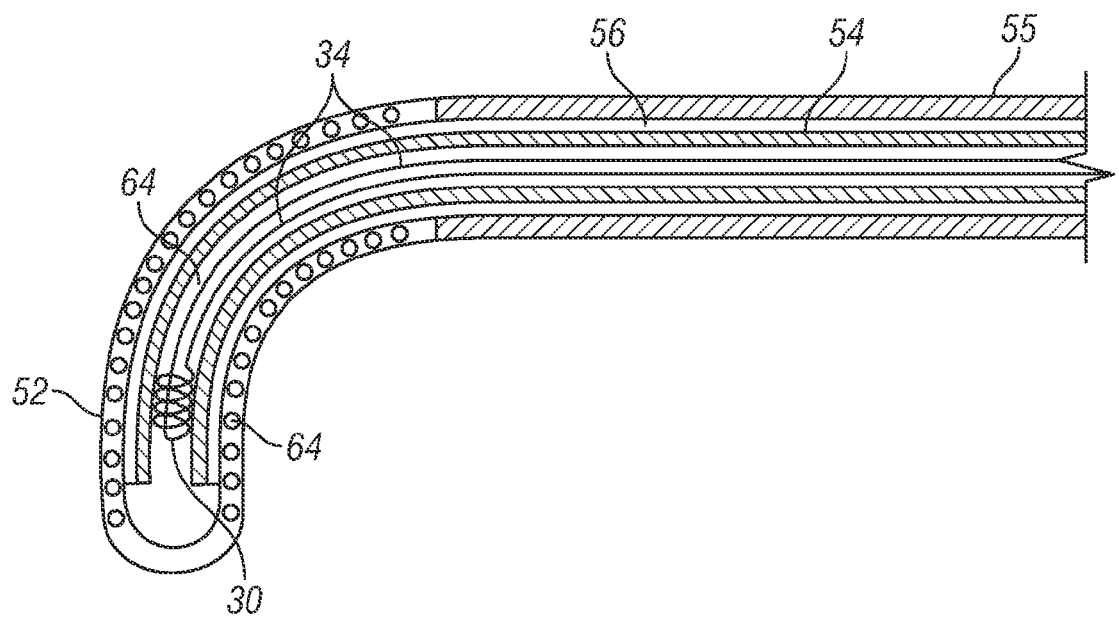
FIG. 4 is an enlarged, cross-sectional view of the distal end portion of the catheter in the bent condition of FIG. 3B.

FIGS. 3A, 3B, and 4 illustrate an alternative embodiment of a deflectable catheter 50 incorporating a tracking coil 30 at a distal end portion 52 of the catheter. The deflectable catheter is similar to the catheter described in co-pending application Ser. No. 11/359,808 filed on Feb. 22, 2006 (US Pat. App. Pub. No. 2006/0142752, the contents of which are incorporated herein by reference. Radio-frequency ("RF") ablation catheter 50 has a shapeable or deflectable antenna apparatus in distal end portion 52 which includes a radio-frequency antenna for delivering electromagnetic energy to a treatment site.

Catheter 50 has a flexible elongated tubular body including coaxial inner and outer tubular conductors 54, 55 separated by a dielectric medium 56. A central lumen 65 extends through the catheter 50 within the inner tubular conductor 54. Located at the proximal portion of the catheter is a handle 58 for housing necessary steering and positioning controls. These controls are described in detail in co pending application Ser. No. 11/359,808 referenced above. Incorporated at a proximal end of the catheter is a coupling 60 for connecting the catheter to the signal processor 36 and RF signal generator 25, as in the system of FIG. 1, in support of ablation and position tracking procedures.

Catheter 50 may be formed with a plurality of segments such that the catheter body is progressively more flexible toward its distal end. The segments may be joined together by thermal bonding, butt joint, or adhesive bonding. Braiding reinforcement can also be added to the circumferential surface of tubular body to attain the desirable level of stiffness and torsional strength for the catheter. This allows the catheter to advance and negotiate through the body vessel of a patient, and to enable torque transfer along the length of the catheter from the proximal portion to the distal portion. The distal portion 52 of catheter body may include a softer polymer compound than the proximal portion, with little or no braiding, to provide the desired flexibility to accommodate distal deflection and shaping of the shapeable antenna apparatus. Deflection and shaping of the shapeable antenna apparatus may be implemented through any of the deflection devices described in co pending application Ser. No. 11/359,808 referenced above, with the deflection controlled by deflection regulating member 62 at handle 58. For example, guide wires (not illustrated) may extend through lumen 65 for connection to locations at the distal end of catheter 50, and may be manipulated by a suitable actuator on handle 58 to control the amount and direction of the deflection of the distal end portion 52.

In the embodiment of FIGS. 3 and 4, a flexible, helically coiled radiating antenna element 64 is embedded in the distal end portion of the catheter for body tissue ablation, as best illustrated in FIG. 4. In a representative embodiment, the RF antenna 64 includes an electrically conductive material or wire strip that is wound in a helical fashion to form a flexible, helical coil winding. The appropriate diameter, pitch and length of the coil winding and the selection of the conductive material or wire strip are a matter of design choice, which can vary according to the particular procedure and flexibility requirements. The helical coil is connected to the RF signal generator 25 via the tubular inner and outer coaxial conductors 54, 55 which are connected to terminals in coupling 60.

As illustrated in FIG. 4, a miniature electromagnetic, inductive tracking sensor coil 30 identical to the tracking coil of the first embodiment, for example an Aurora™ sensor coil as described above in connection with the first embodiment, may be installed in the central lumen 65 at the distal end portion of catheter 50, within the inner conductive tubular member 54, and is connected to terminals in handle via leads 34 extending from the coil through the lumen 65, and from there to the signal processing unit 36 via a suitable cable connected to coupling 60.

Figure 5:
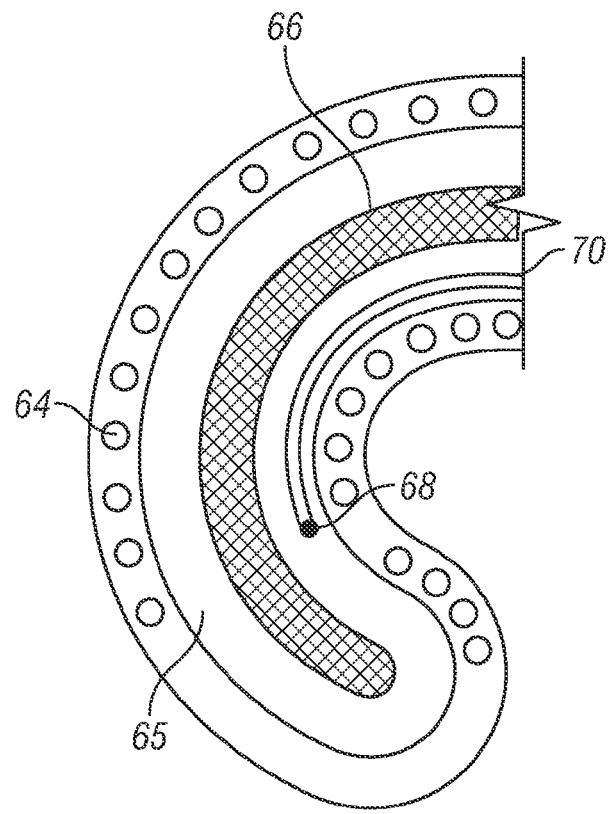
FIG. 5 is a view of the distal tip portion of the catheter in FIG. 4 but illustrating an alternative tracking sensor arrangement.

In an alternative embodiment, instead of inserting a separate inductive or EM tracking coil 30 in the catheter lumen, the antenna coil 64 itself may be used for tracking purposes, as illustrated in FIG. 5. In this case, a flexible, central magnetic core 66 is inserted in lumen 64 to extend coaxially within coil 64, and the core 66 and coil 64 are connected to signal processor terminals in handle 58. As discussed above, the catheter in this embodiment has two different modes of operation, specifically an ablation mode in which the antenna coil is connected to RF signal generator 25 to deliver electromagnetic energy to a treatment site, and a tracking mode in which the coil and central magnetic core are connected to the signal processing module or unit 36, and the separate EM field generator 40 of FIG. 1 is activated to induce a voltage in the resultant inductive coil which is detected and processed by processing module or unit 36. A temperature sensor 68 may also be located in lumen 65 at the distal end portion of catheter 50, and connected by leads 70 to terminals in handle 58 which are in turn connected to signal processing unit 36 for processing in the manner described in co-pending application Ser. No. 11/781,467 filed on Jul. 23, 2007 referenced above, the contents of which are incorporated herein by reference.

Figure 6:
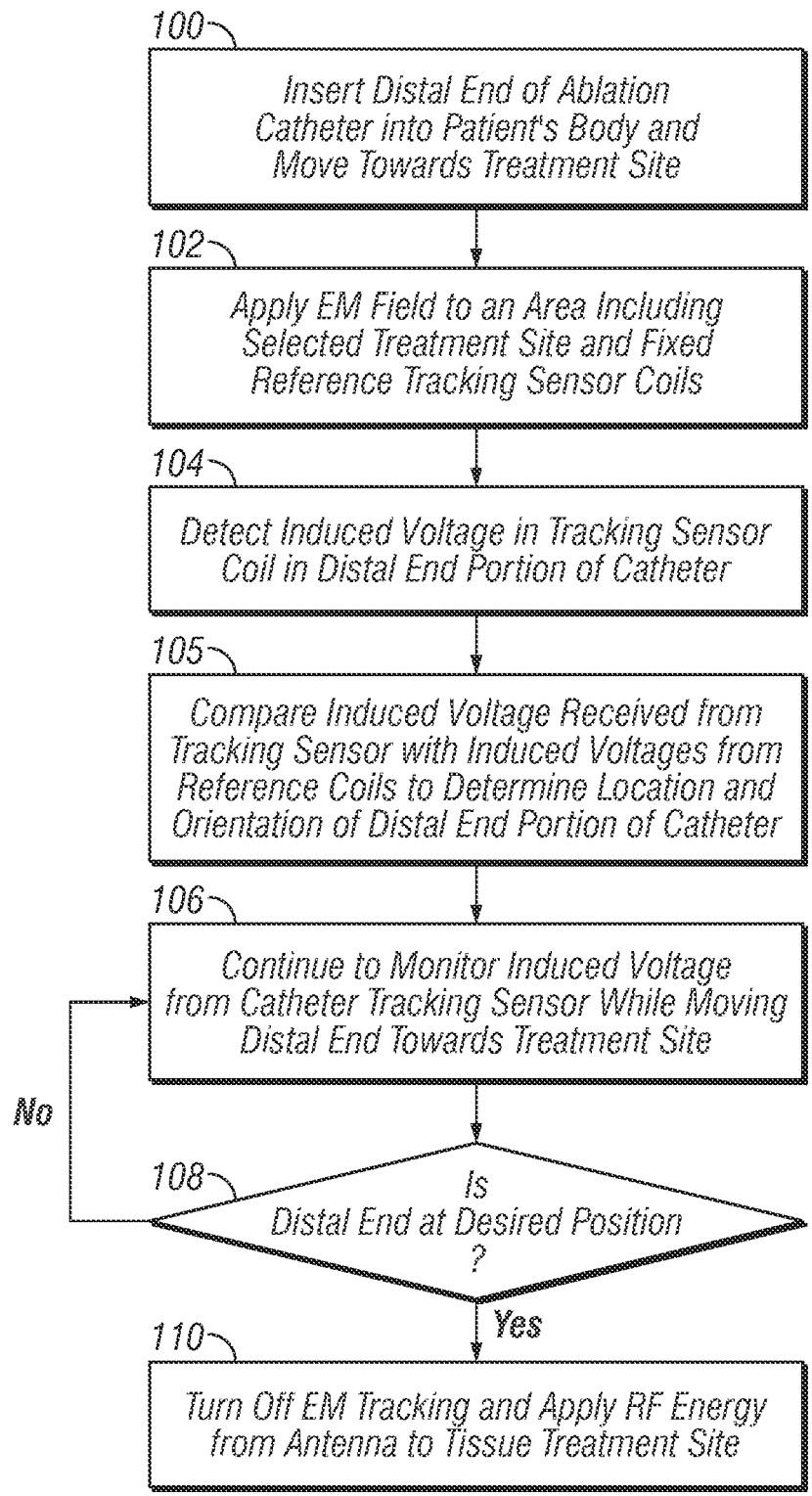
FIG. 6 is a block diagram illustrating one embodiment of a method of positioning the distal end portion of the catheter using the system of FIG. 1 with any of the ablation catheters of FIGS. 2 to 5.

In each of the above embodiments, the tracking coil is used to determine the location of the distal end portion of the catheter or coaxial coil device 10 relative to a target tissue site in a patient's body, as illustrated in FIG. 6. The output of tracking coil 30 or 64 is connected by conductors 34 or alternatively via a wireless link to signal processing unit 36. The distal end of the catheter 10 is then inserted into a patient's body via a body vessel or otherwise and moved to approach a desired treatment site (step 100). It will be understood that the location of the treatment site is determined once the patient is positioned on a treatment table or the like by suitable means such as X-rays, CAT scans or the like, along with the location of reference coils on an operating or treatment table or the like relative to the treatment site, and this information is stored by the processing unit and used to determine an induced voltage output signal corresponding to a desired position of the tracking coil in the distal end portion of the catheter when it is at a selected treatment position adjacent to the treatment site.

As the distal end portion of the catheter continues to moves towards the treatment site, an EM field is applied by EM field generator to an area including the treatment site and reference coils (102). When the coil is within the range of the EM field generated by EM field generator 40, a voltage is induced in the coil and the induced voltage output is monitored by unit 36 (104). The induced voltage is compared with induced voltages received from the reference tracking coils at known positions relative to a patient and the compared voltages are used to determine the location and orientation of the distal end portion of the catheter relative to the desired treatment site (step 105). The distal end portion of the catheter continues to move closer to the treatment site while the signal processing unit monitors the position of the tracking coil (step 106). Once the tracking coil is found to be at the desired position adjacent the treatment site (108), the EM tracking function is turned off and the RF signal generator 25 is turned on so that the antenna applies RF energy for ablation of biological tissue at the treatment site (110). Where the antenna is a helical coil antenna which acts as both the ablation member or antenna and the tracking coil, as in FIG. 5, this step simply involves disconnecting the antenna from the signal processing unit and instead connecting the antenna to the RF signal generator.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

We claim:

1. A radio frequency ablation system, comprising:
    an ablation catheter comprising a hollow conductive coaxial cable having a proximal end portion and a distal end portion, a connector at the proximal end portion of the cable, and an ablation member at the distal end portion of the cable configured to apply radio frequency (RF) energy to a target tissue site;
    the coaxial cable having a first inner elongated electrically conductive tubular member having an axially extending lumen or passageway, a second elongated outer electrically conductive member disposed in a substantially coaxial relationship over at least a portion of the first electrically conductive tubular member, a dielectric medium between the inner and outer conductive tubular members, and at least one electromagnetic tracking sensor located in the lumen at the distal end portion of the cable, the at least one electromagnetic tracking sensor including a sensor coil having a magnetic core;
    an electromagnetic field generator configured for positioning in the vicinity of the patient and generating an electromagnetic field which induces a voltage in the sensor coil when the sensor coil is within the generated electromagnetic field; and
    a signal processing unit comprising at least a signal processor connected to the proximal end portion connector of the coaxial cable, the sensor coil communicating with the signal processor, and the signal processor being configured to detect an induced voltage in the sensor coil and to determine the position and orientation of the distal end portion of the catheter in the patient's body using the induced voltage,
    wherein the ablation member is a helical coil antenna configured to deliver RF energy to a target tissue site of a patient, and a magnetic core is located within the helical coil antenna, whereby the helical coil antenna and magnetic core together comprise the electromagnetic tracking sensor in a tracking mode of the system.

2. An ablation catheter device, comprising:
    a hollow conductive coaxial cable having a proximal end portion and a distal end portion, and a connector at the proximal end portion of the cable;
    the coaxial cable having a first inner elongated electrically conductive tubular member having an axially extending lumen, a second elongated electrically conductive member disposed in a substantially coaxial relationship over at least a portion of the first electrically conductive tubular member, and a dielectric medium between the inner and outer conductive tubular members;
    a combined radio frequency (RF) antenna and tracking sensor disposed at the distal end portion of the coaxial cable and configured to deliver RF energy for the ablation of biological tissue at, a selected tissue site of a patient undergoing treatment in a treatment mode and to provide an output sensor signal to a processing module in a tracking mode;
    the combined RF antenna and tracking sensor comprising a helical coil antenna having a magnetic core and configured to deliver RF energy in the treatment mode and to provide an induced voltage output to a signal processor in the tracking mode when the coil is located within an electromagnetic field generated by an electromagnetic field generator at a predetermined position relative to a target tissue site, whereby the induced voltage output of the tracking sensor coil varies with position and orientation of the distal end portion of the cable relative to a target tissue site.

3. A radio frequency ablation and tracking system, comprising:
    a plurality of reference coils with magnetic cores configured for positioning at known locations in the vicinity of a patient undergoing treatment;
    an ablation catheter configured to supply radio frequency (RF) energy to a target tissue site of the patient, the catheter comprising a hollow conductive coaxial cable having a proximal end portion and a distal end portion, and a connector at the proximal end portion of the cable, the coaxial cable having a first inner elongated electrically conductive tubular member having an axially extending lumen, a second elongated electrically conductive member disposed in a substantially coaxial relationship over at least a portion of the first electrically conductive tubular member, a dielectric medium between the inner and outer conductive tubular members, and at least one electromagnetic tracking sensor coil with a magnetic core located at the distal end portion of the cable;
    an electromagnetic field generator configured for positioning in the vicinity of the patient including a target tissue treatment site of the patient and configured to generate an electromagnetic field which induces a voltage in the reference coils and also inducing a voltage in the tracking sensor coil when the distal end portion of the coaxial cable is in the vicinity of the target tissue site; and
    a signal processor communicating with the tracking sensor coil in the distal end portion of the cable and with the reference coils, the signal processor having a detector module configured to detect an induced voltage in the tracking sensor coil when the distal end portion of the coaxial cable is within the electromagnetic field generated by the electromagnetic field generator, and a processing module configured to determine the location and orientation of the tracking sensor coil based on the detected induced voltage and the known locations of the reference coils,
    wherein the tracking sensor coil further comprises a helical coil antenna configured to transmit radio-frequency energy for ablating biological tissue at a target tissue site of a patient undergoing treatment in a treatment mode of the ablation and tracking system.

* * * * *